(12) United States Patent
Better

(10) Patent No.: US 6,803,210 B2
(45) Date of Patent: Oct. 12, 2004

(54) METHODS AND CELLS FOR EXPRESSION OF RECOMBINANT PROTEIN PRODUCTS UNDER THE TRANSCRIPTIONAL CONTROL OF AN INDUCIBLE PROMOTER

(75) Inventor: Marc D. Better, Oakland, CA (US)

(73) Assignee: XOMA Technology Ltd., Berkeley, CA (US)

( * ) Notice: Subject to any disclaimer, the term of this patent is extended or adjusted under 35 U.S.C. 154(b) by 50 days.

(21) Appl. No.: 09/811,933

(22) Filed: Mar. 19, 2001

(65) Prior Publication Data

US 2002/0037552 A1 Mar. 28, 2002

Related U.S. Application Data

(60) Provisional application No. 60/192,238, filed on Mar. 27, 2000, and provisional application No. 60/192,129, filed on Mar. 24, 2000.

(51) Int. Cl.$^7$ ............................................. C12P 21/02
(52) U.S. Cl. ....................................................... 435/69.1
(58) Field of Search ........................................ 435/69.1

(56) References Cited

U.S. PATENT DOCUMENTS 5,028,530 A   7/1991   Lai et al.

FOREIGN PATENT DOCUMENTS

WO   WO 85/01746   4/1985

OTHER PUBLICATIONS

Albano, et al., "Green Fluorescent Protein as a Real Time Quantitative Reporter of Heterologous Protein Production," *Biotechnol. Prog.* 14:351–354 (1998).
Armengaud, et al., "Production of a full length Tat protein in *E. coli* and its purification," *FEBS Letters,* 282(1):157–160 (Apr. 1991).
Bost, et al., "Transcriptional Activation of ydeA, Which Encodes a Member of the Major Facilitator Superfamily, Interferes with Arabinose Accumulation and Induction of *Escherichia coli* Arabinose $P_{BAD}$ Promoter," *Journal of Bacteriology,* 181(7):2185–2191 (Apr. 1999).
Cagnon, et al., "A new family of sugar–inducible expression vectors for *Escherichia coli*," *Protein Engineering* 4(7):843–847 (Oct. 1991).
Cariello, et al., "A novel bacterial reversion and forward mutation assay based on green fluorescent protein," *Mutation Research,* 414:95–105 (1998).
Carrier, et al., "RNA Stability and Plasmid Copy Number Effects on Gene Expression from an Inducible Promoter System," *Biotechnology and Bioengineering,* 59(6):666–672 (Sep. 20, 1998).
Casadaban, "Fusion of the *Escherichia coli* lac Genes to the ara Promoter: A General Technique Using Bacteriophage Mu–1 Insertions," *Proc. Nat. Acad. Sci. USA,* 72(3):809–813 (Mar. 1975).

Casadaban, et al., "Analysis of Gene Control Signals by DNA Fusion and Cloning in *Escherichia coli*," *J. Mol. Biol.* 138(2):179–207 (1980).
Clark, et al., "Regulation and expression of human fabs under the control of the *Escherichia coli* arabinose promoter, $P_{BAD}$," *Immunotechnology* 3:217–226 (Oct. 1997).
DeLisa, et al., "Monitoring GFP–Operon Fusion Protein Expression During High Cell Density Cultivation of *Escherichia coli* Using an On–line Optical Sensor," *Biotechnology and Bioengineering,* 65(1):54–64 (Oct. 5, 1999).
Doig, et al., "Large scale production of cyclohexanone monooxygenase from *Escherichia coli* TOP10 pQR239," *Enzyme and Microbial Technology,* 28:265–274 (2001).
Dunn, et al., "Deletion Analysis of the *Escherichia coli* ara $P_c$ and $P_{BAD}$ Promoters," *J. Mol. Biol.,* 180:201–204 (1984).
Dunn, et al., "An operator at—280 base pairs that is required for repression of araBAD operon promoter: Addition of DNA helical turns between the operator and promoter cyclically hinders repression," *Proc. Natl. Acad. Sci. USA,* 81:5017–5020 (Aug. 1984).
Greenfield, et al., "DNA sequence of the araBAD promoter in *Escherichia coli* B/r," *Proc. Natl. Acad. Sci. USA,* 75(10):4724–4728 (Oct. 1978).
Guzman, et al., "Tight Regulation, Modulation, and High–Level Expression by Vectors Containing the Arabinose $P_{BAD}$ Promoter," *Journal of Bacteriology,* 177(14):4121–4130 (Jul. 1995).
Hahn, et al., "Upstream Repression and CRP Stimulation of the *Escherichia coli* L–Arabinoise Operon," *J. Mol Biol,* 180(1):61–72 (Nov. 25, 1984).
Haldimann et al., "Use of New Methods for Construction of Tightly Regulated Arabinose and Rhamnose Promoter Fusions in Studies of the *Escherichia coli* Phosphate Regulon," *Journal of Bacteriology,* 180(5):1277–1286 (Mar. 1998).
Hendrickson, et al., "Characterization of the *Escherichia coli* araFGH and araJ Promoters," *J. Mol. Biol.,* 215(4):497–510 (Oct. 20, 1990).
Horazdovsky, et al., "Genetic Reconstitution of the High–Affinity L–Arabinose Transport System," *Journal of Bacteriology,* 171(6):3053–3059 (Jun. 1989).

(List continued on next page.)

Primary Examiner—Terry McKelvey
(74) Attorney, Agent, or Firm—McAndrews, Held & Malloy, Ltd.

(57) ABSTRACT

The present invention relates generally to improved methods for the expression of recombinant protein products under the transcriptional control of an inducible promoter, such as an araB promoter, in bacterial host cells that are deficient in one or more of the active transport systems for the inducer of the inducible promoter. The present invention also relates to improved bacterial host cells that are deficient in one or more of the active transport systems for an inducer of an inducible promoter, such as arabinose for an araB promoter, and contain an expression vector encoding a recombinant polypeptide under the transcriptional control of the inducible promoter, such as an araB promoter.

28 Claims, 4 Drawing Sheets

OTHER PUBLICATIONS

Horazdovsky, et al., "High–Affinity L–Arabionose Transport Operon. Gene Product Expression and mRNAs," *J Mol Biol*, 197(1):27–35 (Sep. 5, 1987).

Horwitz, et al., "Functional Limits of the $araI^c$ Promoter Suggest an Additional Regulatory Site for araBAD Expression," *Journal of Bacteriology*, 158(1):141–147 (Apr. 1984).

Horwitz, et al., "DNA sequence of the araBAD–araC controlling region in *Salmonella typhimurium* LT2," *Gene*, 14(4):309–319 (Sep. 1981).

Huo, et al., "Alternative DNA loops regulate the arabinose operon in *Escherichia coli*," *Proc. Natl. Acad. Sci. USA* 85:5444–5448 (Aug. 1988).

Jacobs, et al., "Human metallothionein–II is synthesized as a stable membrane–localized fusion protein in *Escherichia coli*," *Gene*, 83:95–103 (1989).

Johnson, et al., "In Vivo Induction Kinetics of the Arabinose Promoters in *Escherichia coli*," *Journal of Bacteriology*, 177(12):3438–3442 (Jun. 1995).

Kaplan, et al., "Hybrid Plasmids Containing the araBAD Genes of *Escherichia coli* B/r," *Gene*, 3:177–189 (1978).

Kolodrubetz, et al., "L–arabinose Transport Systems in *Escherichia coli* K–12," *J Bacteriol*, 148(2):472–479 (Nov. 1981).

Kuhn, et al., "Isolation of Mutants in M13 Coat Protein That Affect Its Synthesis, Processing, and Assembly into Phage," *The Journal of Biological Chemistry*, 260(29):15907–15913 (Dec. 15, 1985).

Lechler, et al., "Overproduction of phenylalanyl–tRNA synthetase from *Thermus thermophilus* HB8 in *Escherichia coli*," *Protein Expr Purif* (8):347–357 (Nov. 1996) Article 0110.

Lee, et al., "Arabinose–induced binding of AraC protein to $araI_2$ activates the araBAD operon promoter," *Proc. Natl. Acad. Sci. USA* 84:8814–8818 (1987).

Lee, et al., "Use of Cloned mtl Genes of *Escherichia coli* to Introduce mtl Deletion Mutations into the Chromosome," *Journal of Bacteriology*, 153(2):685–692 (Feb. 1983).

Lee, et al., "Repression of the araBAD Promoter from $araO_1$," *J Mol Biol* 224(2):335–341 (Mar. 20, 1992).

Lin, et al., "The araBAD operon of *Salmonella typhimurium* LT2. II. Nucleotide sequence of araA and primary structure of its product, L–arabinose isomerase," *Gene*, 34(1):123–128 (1985).

Lin, et al., "The araBAD operon of *Salmonella typhimurium* LT2. III. Nucleotide sequence of araD and its flanking regions, and primary structure of its product, L–ribulose–5–phosphate 4–epimerase," *Gene*, 34(1):129–134 (1985).

Lutz, et al., "Independent and tight regulation of transcriptional units in *Escherichia coli* via the LacR/O, the TetR/O and Arac/$l_1$–$l_2$ regulatory elements," *Nucleic Acids Research*, 25(6):1203–1210 (1997).

Maiden, et al., "The Cloning, DNA Sequence, and Overexpression of the Gene araE Coding for Arabinose–Proton Symport in *Escherichia coli* K12*," *The Journal of Biological Chemistry* 263(17):8003–8010 (Jun. 15, 1988).

Maloney, et al., "Distribution of Suboptimally Induced β–D–Galactosidase in *Escherichia coli*," *J. Mol. Biol.*, 73:77–91 (1973).

Miyada, et al., "Five Mutations in the Promoter Region of the araBAD Operon of *Escherichia coli* B/r," *Journal of Bacteriology*, 156(2):765–772 (Nov. 1983).

pBAD. "It does for protein expression what the rheostat did for electricity," *Science*, 1 page, (Aug. 14, 1988).

Perez, et al., "An arabinose–inducible expression vector, pAR3, compatible with ColE1–derived plasmids," *Gene*, 158(1):141–142 (May 26, 1995).

"PGFPuv Vector Information" *Clontech* (updated Apr. 21, 1998) (3 pages).

"Products for Gene Expression and Analysis," *Expressions* 4(4):1–16 (Jun. 1997).

"Pro™ Bacterial Expression System, Multiple levels of control for a wide range of tightly regulated expression," *Clontech* (No dated) 7 pages.

"Pro™ Bacterial Expression System," *Clontechniques* (Oct. 1998) 2 pages.

Reeder, et al., "Mapping, Sequence, and Apparent Lack of Function of araJ, a Gene of the *Escherichia coli* Arabinose Regulon," *Journal of Bacteriology*, 173(24):7765–7771 (Dec. 1991).

Romeyer, et al., "Expression of a *Neurospora crassa* Metallothionein and Its Variants in *Escherichia coli*," *Applied Environmental Microbiology*, 56(9):2748–2754 (Sep. 1990).

Saviola, et al., "Arm–Domain Interactions in AraC," *J. Mol Biol*, 278(3):539–548 (May 8, 1998).

Schleif, "L–Arabinose Operon Messenger of *Escherichia coli*," *J. Mol. Biol.* 61(1):275–279 (1971).

Schleif, et al., "Dual Control of Arabinose Genes on Transducing Phage λdara," *J. Mol. Biol.* 59:127–150 (1971).

Schleif, et al., "Transcription in the Lambda–ara Phage," *Transcription of Genetic Material*, Cold Spring Harbor Symposia on Quantitative Biology vol. XXXV, pp. 369–373 (1970).

Scripture, et al., "High–affinity L–arabinose transport operon. Nucleotide Sequence and analysis of gene products," *J Mol Biol*, 197(1):37–46 (1987).

Siegele, et al., "Gene expression from plasmids containing the araBAD promoter at subsaturating inducer concentrations represents mixed populations," *Proc. Natl. Acad. Sci. USA*, 94:8168–8172 (Jul. 1997).

Slos, et al., "Recombinant cholera toxin B subunit in *Escherichia coli*: high–level secretion, purification, and characterization," *Protein Expr Purif*, 5(5):518–526 (Oct. 1994).

Stoner, et al., "The araE low affinity L–arabinose transport promoter. Cloning, sequence, transcription start site and DNA binding sites of regulatory proteins," *J. Mol. Biol*, 171(4):369–381 (Dec. 25, 1983).

Taylor, et al., "High–level expression and purification of mature HIV–1 protease in *Escherichia coli* under control of the araBAD promoter," *Appl Microbial Biotechnol* 37(2):205–210 (May 1992).

Wilcox, et al., "Interaction of the Regulatory Gene Produce with the Operator Site in the L–Arabinose Operon of *Escherichia coli*," *J. Mol. Biol.*, 85:589–602 (1974).

Carrier, et al., "Investigating Autocatalytic Gene Expression Systems Through Mechanistic Modeling" *J.Theor. Biol.* 201:25–36 (1999).

Hahn, et al., "In Vivo Regulation of the *Escherichia coli* araC Promoter" *J. Bacteriol.*, 155(2):593–600 (Aug. 1983).

Klebnikov, et al., "Regulatable Arabinose–Inducible Gene Expression System with Consistent Control in all Cells of a Culture," *J. Bacteriol.*, 182(24):7029–7034.

| Lane 1 | Transductant 1 | 0.01% arabinose |
| Lane 2 | Transductant 2 | 0.01% arabinose |
| Lane 3 | Transductant 3 | 0.01% arabinose |
| Lane 4 | Transductant 4 | 0.01% arabinose |
| Lane 5 | Transductant 5 | 0.01% arabinose |
| Lane 6 | E220 | 0.01% arabinose |
| Lane 7 | E226 | 0.01% arabinose |
| Lane 8 | Transductant 2 | 1.0% arabinose |
| Lane 9 | Transductant 3 | 1.0% arabinose |
| Lane 10 | Transductant 5 | 1.0% arabinose |
| Lane 11 | E220 | 1.0% arabinose |
| Lane 12 | E226 | 1.0% arabinose |

| | | |
|---|---|---|
| Lane 1 | W3110 | 0.01% arabinose |
| Lane 2 | E220 | 0.01% arabinose |
| Lane 3 | E224 | 0.01% arabinose |
| Lane 4 | E226 | 0.01% arabinose |
| Lane 5 | W3110 | 0.1% arabinose |
| Lane 6 | E220 | 0.1% arabinose |
| Lane 7 | E224 | 0.1% arabinose |
| Lane 8 | E226 | 0.1% arabinose |
| Lane 9 | W3110 | 1.0% arabinose |
| Lane 10 | E220 | 1.0% arabinose |
| Lane 11 | E224 | 1.0% arabinose |
| Lane 12 | E226 | 1.0% arabinose |

| Lane 1 | Size Standard | |
|---|---|---|
| Lane 2 | E220 | uninduced |
| Lane 3 | E226 | uninduced |
| Lane 4 | E220 | 0.01% arabinose |
| Lane 5 | E224 | 0.01% arabinose |
| Lane 6 | E226 | 0.01% arabinose |
| Lane 7 | E220 | 0.1% arabinose |
| Lane 8 | E224 | 0.1% arabinose |
| Lane 9 | E226 | 0.1% arabinose |
| Lane 10 | E220 | 1.0% arabinose |
| Lane 11 | E224 | 1.0% arabinose |
| Lane 12 | E226 | 1.0% arabinose |

METHODS AND CELLS FOR EXPRESSION OF RECOMBINANT PROTEIN PRODUCTS UNDER THE TRANSCRIPTIONAL CONTROL OF AN INDUCIBLE PROMOTER

This application claims priority of U.S. Provisional Application Nos. 60/192,238 filed Mar. 27, 2000 and 60/192,129 filed Mar. 24, 2000, the disclosures of which are incorporated by reference herein.

The present invention relates generally to improved methods for the expression of recombinant protein products under the transcriptional control of an inducible promoter, such as the araB promoter, in bacterial host cells that are deficient in one or more of the active transport systems for an inducer. In the case of the araB promoter, the inducer is L-arabinose. The present invention also relates to improved bacterial host cells that are deficient in one or more of the active transport systems for an inducer, such as L-arabinose, and that contain an expression vector encoding a recombinant protein product under the transcriptional control of an inducible promoter, such as the araB promoter.

BACKGROUND OF THE INVENTION

Although many systems have been described for expression of recombinant proteins, including peptides and polypeptides, in microbial systems, most gene expression systems in gram negative bacteria such as *Escherichia coli* have relied exclusively on a limited set of bacterial promoters. The most widely used bacterial promoters have included the lactose [lac] (Yanisch-Perron et al., 1985, *Gene* 33: 103–109), and the tryptophan [trp] (Goeddel et al., 1980, *Nature* (London) 287: 411–416) promoters, and the hybrid promoters derived from these two [tac and trc] (Brosius, 1984, *Gene* 27: 161–172; and Amanna and Brosius, 1985, *Gene* 40: 183–190). Other commonly used bacterial promoters include the phage lambda promoters $P_L$ and $P_R$ (Elvin et al., 1990, *Gene* 37: 123–126), the phage T7 promoter (Tabor and Richardson, 1998, *Proc. Natl. Acad. Sci. U.S.A.* 82: 1074–1078), and the alkaline phosphatase promoter [pho] (Chang et al., 1986, *Gene* 44: 121–125). Each of these promoters has desirable features. However, the ideal promoter for expression of a wide variety of recombinant proteins would offer certain features not found in these commonly used systems. For example, many recombinant products can be toxic to the expression host. Therefore, it is often preferable for the promoter to tightly regulate gene expression during culture propagation when gene expression is undesirable. In contrast, when gene expression is desired, the promoter must be easily controlled and a high expression level is often preferred. The agent or environmental condition that initiates gene expression should be easy to use and ideally of low cost. In general, a tightly regulated system is most desirable. Features of a promoter and general expression system that are most preferred include tightly repressed gene expression in the absence of inducer and highly derepressed gene expression in the presence of inducer. Also desirable would be a system that will allow the expression level of a recombinant product to be proportional to the amount of inducing agent added into the cell culture.

One bacterial promoter system that has proven to be particularly advantageous for providing tightly repressed gene expression in the absence of the inducer arabinose and highly derepressed gene expression in the presence of the inducer arabinose is the araB promoter of the Enterobacteriaceae family. Of interest is U.S. Pat. No. 5,028,530, which is hereby incorporated by reference, which describes the use of the araB expression system for production of polypeptides, including cecropins, by microbiological techniques. Two features of the ara system have made it particularly well-suited for expression of recombinant products in bacteria such as *E. coli*. First, it is simple to exploit because the control elements of the araB promoter are conveniently contained within an approximately 300 base pair regulatory region and only a functional coding sequence for the araC gene is additionally needed. Second, regulation of the system has proven to be particularly tight, i.e., the ratio of the amount of product in the induced state (with arabinose) relative to that in the repressed state (without arabinose) from the araB promoter on multicopy expression plasmids is relatively high, most frequently in the range from >200–75,000 (Better et al., 1999, in *Gene Expression Systems: Using Nature for the Art of Expression*, Academic Press, New York, pp. 95–107). Additionally, the uninduced level of protein expression from the ara system is very low. This feature is particularly important and useful when protein products, including recombinant peptides and polypeptides, that are toxic to the host are to be expressed.

Bacteria such as *E. coli* have two known systems for active transport of arabinose into the cell. The first of these systems is an inducible, energy-dependent accumulation process catalyzed by the product of the araE gene. The araE gene product is an approximately 52,000 Da, membrane-associated protein that constitutes the low affinity arabinose transport system (Maiden et al., 1988, *Journal of Biol. Chem.* 263: 8003–8101). The second L-arabinose transport system has a greater affinity for L-arabinose and is dependent on the activity of the L-arabinose binding protein, AraF. The locus encoding this arabinose binding protein, araF, is part of an operon with araG and araH. The protein products from these three genes, araFGH, make up the high affinity L-arabinose transport system (Horazdovsky and Hogg, 1989, *Jour. of Bacter.* 171: 3053–3059). Arabinose transport-deficient mutant *E. coli* strains have been prepared (see, e.g., Maiden et al., supra; Harazdovsky and Hogg, supra).

Of interest are the disclosures of the following references which relate to use of the araB promoter for expression of polypeptides in bacteria.

Johnston et al., 1985, *Gene* 34: 137–145, described the vector pING1 which contained the ara regulatory region, the complete araC gene and a portion of the araB gene from *S. typhimurium*. Restriction sites were introduced into the coding region of araB gene so that a gene fusion or a multigene transcription unit could be expressed under arabinose control. This system was used to express homologous (bacterial) proteins which normally are expressed in *E. coli* under certain circumstances, namely the M13 gene II (Johnson et al., 1985) and gene 8 proteins (Kuhn and Wickner, 1985, *J. Biol. Chem.* 260: 15907–15918), and a similar vector were used to express the RepE protein from the *E. coli* F plasmid (Masson et al., 1986, *Nucleic Acids Res.* 14: 5693–5711). Each of these proteins was produced in the cytoplasm of *E. coli* cells, and at least some of the expressed protein was soluble and could be detected in an active form either in vivo or in cell extracts.

Better et al., 1988, *Science* 240: 1041–1043, described an araB expression system derived from pING1 that was subsequently engineered to regulate the expression of heterologous (non-bacterial) recombinant proteins. Heterologous proteins successfully produced with the araB expression system in *E. coli* include immunoglobulin Fab domains. In this case, the araB expression system was used to direct the production of polypeptides directly linked to hydrophobic signal sequences through the bacterial cytoplasmic membrane where Fab accumulated in the correctly folded, fully active configuration and could be recovered directly from the culture supernatant. Expression of Fab domains under the transcriptional control of the araB promoter was the first demonstration that a heterodimeric, heterologous protein could be produced in E. coli. The initially reported expression level was approximately 1–2 μg/mL, but in subsequent studies the level of protein expression could be increased nearly 1000-fold by growing the bacteria to a high cell density in a fermentor (Better et al., 1990, ICSU Short Rep. 10: 105). In contrast, Clark et al., 1997, Immunotechnology 3: 217–226, found that Fab genes under lac control can inhibit bacterial growth, and also that Fab expression from $P_{BAD}$ was more tightly repressed than that from $P_{lac}$.

Better et al., 1992, J. Biol. Chem. 267: 16712–16718; Nolan et al., 1993, Gene 134: 223–227; and Bernhard et al., 1994, Bioconjugate Chem. 5: 126–132, showed that the araB expression system could be used successfully for the production of other proteins. Several plant and fungal ribosome-inactivating proteins were expressed under direct control of arabinose in E. coli. One such protein, gelonin, was expressed as a secreted protein in E. coli and accumulated to greater than 1 g/L as a fully active protein in the cell-free culture supernatant. Fusion proteins between antibody domains that can target antigens on human cells and cytotoxic molecules such as gelonin were also expressed under the transcriptional control of arabinose, Better et al., 1995, J. Biol. Chem. 270: 14951–14957. These immunofusion proteins accumulated in the cell-free culture supernatant from arabinose-induced cells at greater than 400 mg/L. Members of a family of immunofusion proteins expressed in E. coli under the transcriptional control of the araB promoter retained both in vitro and in vivo biological activity comparable to that of chemically prepared immunoconjugates made from animal cell-produced whole antibodies and ribosome-inactivating proteins purified directly from plants.

Jacobs et al., 1989, Gene 83: 95–103 and Romeyer et al., 1990, Appl. Environ. Microbiol. 56: 2748–2754, also used plasmids derived from pING1 to encode mammalian proteins that can become localized in the outer cell membrane of bacteria. In one example, a human metallothionein-II gene was linked to the leader and membrane-association fragment of the E. coli lipoprotein Lpp (Jacobs et al., 1989). When induced with arabinose, bacteria carrying this expression vector directed an active metallothionein protein to the outer cell membrane. The recombinant protein was produced at ~75,000-fold over the uninduced level. This system was used to express an active heterologous protein that previously had been somewhat toxic and unstable in E. coli.

Cagnon et al., 1991, Protein Eng. 4: 843–847, described a series of expression vectors that contained the ara expression system from pING1 in the vector pKK233.2 along with a number of other optional features. In the Cagnon series of expression vectors, the promoter/operator region of araB was followed by a polylinker region for convenient gene cloning. In addition, some vectors contained synthetic signal sequences, an f1 phage origin of replication, and mutated araB promoter sequences. The mutated araB promoter incorporated changes in the −10 region that made the promoter match more closely a consensus E. coli promoter. The promoter mutations resulted in higher level of inducible expression (2-fold) for a marker gene, however, the uninduced expression level increased as well. Several recombinant proteins were expressed from this family of ara expression vectors including the full length Tat protein from the HIV virus (Armengaud et al., 1991, FEBS Lett. 282: 157–160) and the bacterial proteins: β-galactosidase (Cagnon et al., 1991), the Streptoalloteichus hindustanus bleomycin-binding protein (Cagnon et al., 1991), and the cholera toxin subunit B (Slos et al., 1994, Protein Express. Purif. 5: 518–526). The cholera toxin subunit B (CT-B) was linked to the ompA signal sequence and expressed as a secreted protein. CT-B accumulated to approximately 60% of the total periplasmic protein and CT-B was produced at about 1 g/liter at pilot scale. The majority of CT-B was released into the culture medium and could be recovered at greater than 80% efficiency from the cell-free culture medium.

Perez-Perez and Gutierrez, 1995, Gene 158: 141–142, described an ara expression system in pACYC184 that remains compatible with ColE1-derived plasmids in an expression host.

Guzman et al., 1995, J. Bacteriol. 177: 4121–4130, described a series of araB expression vectors that incorporate various selectable markers and multicloning sites. This series of vectors was studied extensively for the expression of native E. coli proteins. Guzman et al. (1995) also presented evidence that the araB system can be used "to achieve very low levels of uninduced expression, obtain moderately high levels of expression in the presence of inducer, and modulate expression over a wide range of inducer concentrations."The possibility was raised that the extent of arabinose induction can be regulated by the amount of inducer added to the culture.

Others have reported that gene expression under the control of the araB promoter appeared to be directly regulated by the concentration of arabinose introduced into the culture medium (Lutz and Bujard, 1997, Nucleic Acids Research 25: 1203–1210; and Carrier et al., 1998, Biotechnol. Bioengineering 59: 666–672). However, in contrast, Siegele and Hu, 1997, Proc. Natl. Acad. Sci. U.S.A. 94: 8168–8172, demonstrated that gene expression from plasmids containing the araB promoter at subsaturating arabinose concentrations actually represent the population average of mixed populations of induced and uninduced cells. Thus, intermediate expression levels in culture simply reflected the average of the induced and uninduced cells in the population, not direct regulation. Siegele and Hu, supra, constructed plasmids that contained a reporter gene for a mutated green fluorescent protein (gfp), and those plasmids expressed a fast-folding mutant of the Aequorea victoria green fluorescent protein under the transcriptional control of the araB promoter. Microscopic examination of cells grown at low arabinose concentrations showed a mixture of brightly fluorescent and dark cells, suggesting that intermediate expression levels in cultures reflect a population average. Because the inducer arabinose is actively transported into the cell, the amount of induction in any given cell would be expected to vary with the amount of arabinose actively transported into that cell. Thus, the average amount of induction in a population of cells would, in turn, represent the average amount of arabinose actively transported into that population of cells. It is important to note, however, that those cells that do contain high concentrations of arabinose are fully induced. A similar phenomenon has also been reported with lactose transport and the induction of the lac operon (Novick and Weiner, 1957, Proc. Natl. Acad. Sci. USA 43: 553 and Maloney and Rotman, 1973, J. Mol. Biol. 73: 71–91). Thus, these references, including Siegele and Hu, supra, conclude that although araB vectors have the advantages of rapid regulation and low basal level expression compared to plasmids regulated by the lac repressor, the araB promoter is not well-suited to modulate the expression of cloned genes because of variances in arabinose uptake between cells.

The references cited above indicate that the araB expression system is useful for the controlled expression of recombinant proteins in bacterial systems. These references further indicate that the araB system offers advantages not found in other bacterial expression systems. However, a problem still facing the art is to generate directly regulated cell cultures in which the amount of protein expression in the cells is actually proportional to the amount of inducer (e.g., arabinose) present in culture medium. Because induction of recombinant products in bacterial cells can often inhibit subsequent cell growth, it would be desirable to generate cell cultures in which gene expression could be regulated directly and proportionally by the amount of inducer present.

SUMMARY OF THE INVENTION

The present invention is directed to improved methods for the expression of recombinant protein products, including peptides and polypeptides, under the transcriptional control of an inducible promoter, such as the araB promoter. According to the invention, bacterial host cells are genetically engineered with deficiencies in active transport system (s) for an inducer of a promoter contain vectors for the expression of recombinant protein products under the transcription control of an inducible promoter. The present invention specifically provides novel genetically engineered bacterial host cells, that are genetically deficient in one or both of the two known L-arabinose transport systems in *E. coli* and related bacteria of the Enterobacteriaceae family, including species of Salmonella, Pseudomonas, Proteus and Enterobacter, and capable of expressing recombinant protein products. Use of such transport-deficient bacterial host cells, including arabinose transport-deficient bacterial host cells, for the expression of recombinant protein products under the transcriptional control of an inducible promoter such as the araB promoter provides, for increased expression of the recombinant protein product, lower inhibition of host cell growth after induction, and/or direct and synchronous induction of expression in such host cells as compared to that in the transport-proficient cells. Recombinant protein products, including protein products useful as therapeutic, prophylactic and/or diagnostic agents, are thus efficiently and economically produced according to the methods of the present invention.

The present invention provides a method for producing a recombinant protein product under the inducible control of an inducible promoter, such as an araB promoter, comprising: (a) introducing a recombinant expression vector encoding a recombinant protein product under the control of an inducible (e.g., araB) promoter into a bacterial host cell that is genetically deficient in at least one system for active transport of the inducer (e.g., arabinose) into the host cell; and (b) inducing expression of the recombinant protein product with the inducer (e.g., arabinose).

According to the invention, an improved method provides direct regulation, including synchronous induction, of bacterial cell cultures, in which expression of recombinant protein product is proportional to the culture concentration of the inducer, (e.g., arabinose). In genetically engineered host cells according to the invention that contain a vector for protein product expression under the transcription control of the inducible (e.g., araB) promoter and that are deficient in inducer (e.g., arabinose) transport, the intracellular concentration of the inducer (e.g., arabinose) is proportional to the concentration of the inducer (e.g., arabinose) in the culture medium because passive diffusion is the only mechanism for intracellular accumulation of the inducer (e.g., arabinose) across the bacterial membranes. This is direct regulation of expression and leads to synchronous induction of recombinant protein product expression in the host cells. Thus, the methods of the present invention offer advantages not found with expression in transport-proficient bacterial hosts from an inducible promoter, such as the araB promoter, where there is a mixed population of induced and uninduced cells, and where the apparent relationship between the amount of recombinant product and the concentration of inducing agent at subsaturating amounts of the inducer, such as arabinose, reflects the population average of expression in both induced and uninduced cells.

The present invention also provides a bacterial host cell that is deficient in one or more of the active transport systems for an inducer, such as L-arabinose, and that contains an expression vector encoding a recombinant protein product under the transcriptional control of an inducible promoter, such as the araB promoter. Such cells are useful for the production of a variety of protein products. According to the invention, recombinant protein products may be therapeutic, prophylactic and/or diagnostic agents. Such recombinant products may include protein products, preferably animal and plant derived products, that are not reporter or marker gene products, including mammalian gene products such as human or human-like protein products.

BRIEF DESCRIPTION OF THE FIGURES

FIG. 2A shows induction after 4 hours;

FIG. 2B shows induction after 18 hours.

DETAILED DESCRIPTION OF THE INVENTION

Figure 1:
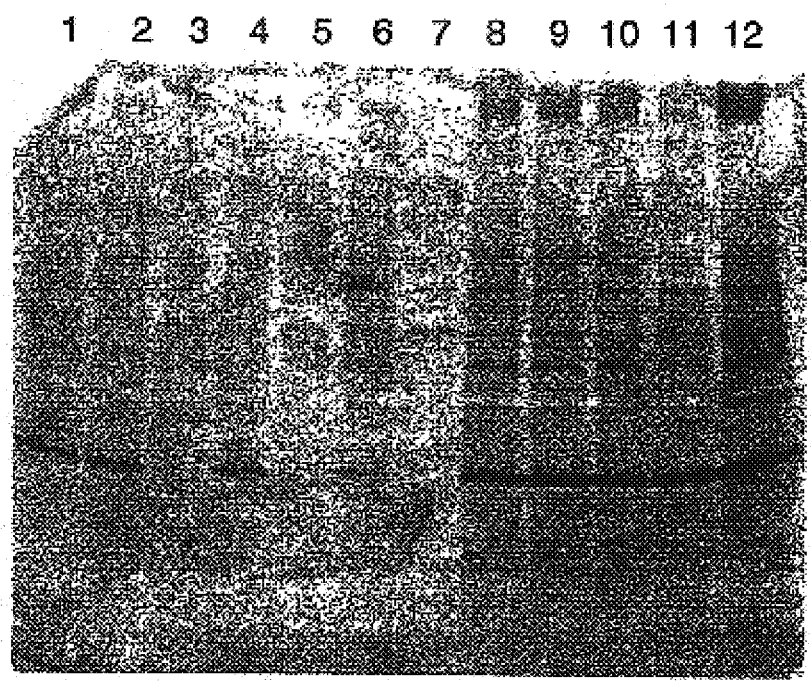
FIG. 1 shows a silver stained polyacrylamide gel that compares protein pattern after induction of E220 (pING3825), E226 (pING3825) and E229 (pING3825) transformants after induction with 0.01 and 1.0% arabinose for 4.5 hours.

Methods of the present invention are based upon the surprising discovery that the level of expression of recombinant protein products expressed under the transcriptional control of an inducible promoter, such as the araB promoter, can be higher in bacterial cells that are deficient in at least one active transport system for the inducer of the promoter, such as in one or both of the arabinose transport systems of *E. coli*. Also, surprisingly, substantial decreases in bacterial cell growth inhibition of such transport-deficient host cells are achieved compared to that in transport-proficient cells. For example, with arabinose, such decreases in growth inhibition due to arabinose can be observed using approximately 10–100 fold higher arabinose concentrations with such transport-deficient cells, with recombinant protein expression to approximately the same or greater level. Additionally, direct regulation and synchronous induction of recombinant protein expression with an inducer such as arabinose was surprisingly demonstrated in such host cells. The present invention is generally directed to improved methods for the expression of recombinant protein products under the transcriptional control of an inducible promoter, such as the araB promoter, in bacterial host cells that are deficient in one or more of the active transport systems for an inducer, such as L-arabinose, whereby gene expression under the control of the inducible promoter can be directly regulated by the concentration of the inducer, such as arabinose, present in the culture medium. Concentrations of arabinose useful to induce host cells include about 0.00001% to about 10% (v/v). The present invention is also generally directed to bacterial host cells that are deficient in one or more of the active transport systems for an inducer of a promoter, such as L-arabinose, containing an expression vector encoding a recombinant protein product under the transcriptional control of an inducible promoter, such as the araB promoter. Increased expression of a recombinant protein product is provided by such a bacterial host cell according to the invention.

The present invention thus provides improved methods for the expression of recombinant protein products under the transcriptional control of an inducible promoter, such as the araB promoter, in bacterial host cells that are deficient in one or more of the active transport systems for an inducer, such as L-arabinose. Gene expression under the control of such an inducible promoter (e.g., araB) can be directly regulated by the concentration of inducer (e.g., arabinose) present in the culture medium. In particular, the method specifically provides the development and use of bacterial host cells containing expression vectors encoding recombinant protein products, where the cells are genetically deficient in one or both of the two known L-arabinose transport systems in $E.$ $coli$ or similar arabinose transport systems in any of the related bacteria of the Enterobacteriaceae family. Use of arabinose transport-deficient strains for the expression of recombinant protein products under the transcriptional control of the araB promoter provided for an increased expression of recombinant product and/or lower inhibition of host cell growth after induction compared to expression levels in arabinose transport-proficient cells. Thus, the method of the invention is useful to increase the yield of cells and/or recombinant protein product from induced bacterial host cells. The improved method also provides a means to directly regulate the amount of recombinant protein product in a host cell by controlling the amount of the inducing agent, such as L-arabinose, that is introduced into the bacterial culture.

"Vector" refers to plasmid or viral DNA that contains recombinant genetic material which encodes a recombinant protein product(s) and may be capable of autonomous replication in bacteria. Vector is also referred to herein as "recombinant expression vector" or "expression vector".

"Transformation" or "transformed" refers to an introduction of recombinant genetic material such as a vector (e.g., plasmid) into a bacterial cell by any transformation method known in the art. A bacterial cell or those colonies resulting from a bacterial cell that have received such recombinant genetic material are referred to as "transformants".

"Transduction" or "transduced" refers to the introduction of genetic material into a bacterial host from the genetic material of a bacteriophage by any transduction method known in the art. A bacterial cell or those colonies resulting from a bacterial cell that have received such a segment of genetic material from a bacteriophage are referred to as "transductants."

"Genetically deficient" refers to a lack of or deficiency of a gene product by mutation of DNA, including by substitution, deletion and/or addition.

"Recombinant protein product" refers to any protein product that is not a reporter or marker gene product (such as a green fluorescent protein) expressed from recombinant genetic material encoding amino acids, including peptides, polypeptides, proteins, oligoproteins and/or fusion proteins. A recombinant protein product is preferably an animal or plant derived product that is not a reporter or marker gene product such as a green fluorescent protein. A recombinant protein product is preferably a mammalian or plant derived recombinant product. A recombinant protein product is also preferably a human or human-like protein product. A recombinant protein product is preferably a therapeutic, prophylactic or diagnostic product. "Reporter gene product" or "marker gene product" refer to research tools that are readily detectable protein products that are commonly used to study whether gene expression has occurred (i.e., act as reporters or markers of their expression). Representative reporter or marker gene products include chloramphenicol acetyl transferase (CAT), bovine pancreatic trypsin inhibitor (BPTI), B-lactamase (B-lac), B-galactosidase (B-gel) and various forms of green fluorescent protein (gfp).

The protein "gelonin" refers to the ribosome inactivating protein gelonin, expressed herein as a recombinant product under the transcriptional control of the araB promoter. The recombinant protein gelonin was cloned from the seed of the plant $Gelonium$ $multiflorum$ as described in Nolan et al., 1993, $Gene$ 134: 223–227, and as described in co-owned U.S. Pat. Nos. 5,376,546 and 5,837,491, which are hereby incorporated by reference. Gelonin was expressed as a secreted protein in $E.$ $coli$ using the pelB leader sequence, which leader sequence is described in co-owned U.S. Pat. Nos. 5,576,195 and 5,846,818, which are hereby incorporated by reference.

The recombinant gelonin protein product expressed according to the invention is an exemplary recombinant protein product expressed in an exemplary bacterial host cell ($E.$ $coli$) under the transcriptional control of an examplary inducible promoter (the araB promoter). Expressed recombinant protein products of the invention can include any amino acid sequences known in the art for such recombinant protein products that are not a reporter or marker gene product such as a green fluorescent protein under the transcriptional control of an inducible promoter, preferably the araB promoter. The invention provides for recombinant protein products that accumulate in any bacterial compartment or are secreted into the cell-free culture supernatant after induction of the inducible (e.g., araB) promoter. Thus, the invention relates to, but is not limited to, those recombinant protein products that remain associated with the bacterial host cells after induction either in the periplasm or cytoplasm, or those that are secreted into the culture medium.

Figure 4:
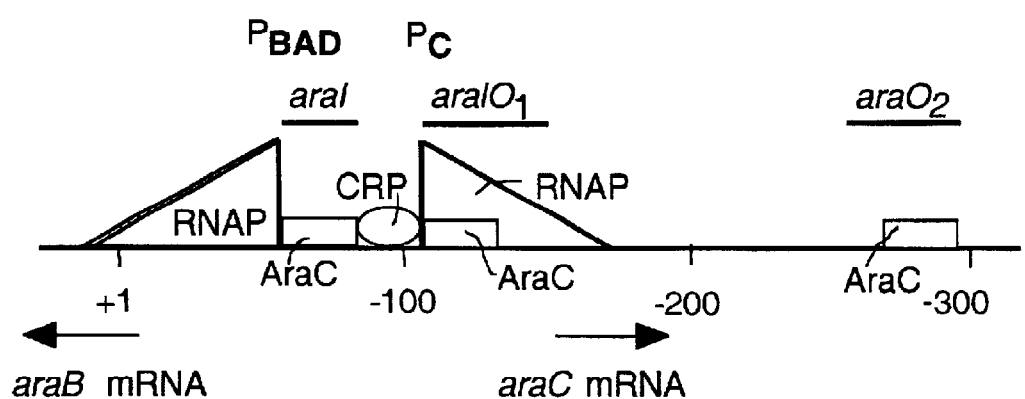
FIG. 4 shows a schematic of the araB promoter system (see also, Better et al., 1999 supra).

The araB promoter useful according to the invention is an exemplary inducible promoter. An inducer of this inducible promoter is arabinose, a five carbon sugar that is found widely in nature that can serve as a sole carbon source in many bacteria for the growth. This inducible promoter system is reviewed in Better et al., 1999, supra. The protein products from three genes (araB, araA, and araD) are needed for arabinose degradation in members of the Enterobacteriaceae family, such as $E.$ $coli$ and $S.$ $typhimurium$, and these genes form a cluster abbreviated araBAD. These genes are arranged in a single operon and encode the enzymes ribulokinase (AraB), L-arabinose isomerase (AraA) and L-ribulose-5-phosphate-4 epimerase (AraD). Adjacent to the araBAD operon is a complex promoter region and the regulatory gene araC. The araBAD and araC genes are transcribed in opposite directions. Within and around the promoters for araBAD ($P_{BAD}$) and araC ($P_C$) lie binding sites for the AraC protein, the cyclic AMP receptor protein (CRP), and RNA polymerase. Alone or in combination, proteins bound to these regions both in the presence or absence of the inducer, L-arabinose, tightly regulate expression from both promoters. FIG. 4 illustrates the spatial arrangement of regulatory sites within this complex araBAD and araC promoter region.

Transcription from the $P_{BAD}$ is inducible with L-arabinose. In the presence of arabinose, AraC protein bound at the araI site immediately adjacent to the RNA polymerase binding site of the $P_{BAD}$ promoter stimulates transcription of the araBAD operon. In the absence of arabinose, however, the AraC protein represses mRNA synthesis from $P_{BAD}$ by a mechanism involving the formation of a DNA loop. Without arabinose, most copies of the ara regulatory region contain a DNA loop between the $araO_2$ and araI sites mediated by AraC protein bound to both of these sites. This loop constrains AraC protein bound at araI from entering the inducing state, and holds the uninduced level of $P_{BAD}$ expression low. Upon the addition of arabinose, the $araO_2$-araI loop opens, and arabinose bound to AraC protein on the araI site drives AraC into the inducing conformation, thereby inducing $P_{BAD}$. Regulation of this operon is also subject to catabolite repression, so even in the presence of arabinose, significantly less induction occurs when intracellular cyclic AMP (cAMP) levels are low, such as when the cells are grown in the presence of glucose.

Transcription from $P_C$ is also regulated by arabinose. In the absence of arabinose, access of RNA polymerase to $P_C$ is limited by formation of the AraC-mediated araI-$araO_2$ loop, and araC expression remains low. In the presence of arabinose, AraC bound to araI in its inducing conformation relieves the steric constraint and RNA polymerase has increased access to $P_C$. Transcriptional activity of $P_C$ is transient, however, as AraC can bind to $araO_1$ and AraC-mediated DNA loops form between $araO_1$ and $araO_2$ that ultimately limit transcription from $P_C$. In addition, $P_C$ is also subject to catabolite repression.

Although seemingly complex, these regulatory arrangements allow bacteria to produce enzymes for arabinose metabolism only when they are needed. The system has evolved to include two positive regulatory proteins (AraC+ arabinose; CRP), one negative regulatory element (AraC− arabinose), a mechanism to control gene expression through DNA looping, and a system that can prevent or enhance an interaction with RNA polymerase. All of the features of this entire regulatory region are conveniently contained within about 300 base pairs of DNA as shown in FIG. 4.

Thus an "araB promoter" refers to a control region of DNA containing at least one binding site for an RNA polymerase and associated binding site(s) for AraC protein or its functional equivalent. Essential control elements of an araB promoter of the Enterobacteracae family exemplified by that of E. coli are found in the DNA corresponding to the approximately +1 to −100 region of the promoter as depicted schematically in FIG. 4. Additional preferred control elements such as additional binding site(s) for araC or its functional equivalent (e.g., $AraO_2$) are found in the DNA corresponding to the approximately −100 to −300 region of the promoter as also depicted schematically in FIG. 4. Most preferably, an araB promoter refers to the control region of DNA corresponding to the approximately +1 to −300 region of the promoter as depicted schematically in FIG. 4.

Bacterial host cells of the invention may be propagated by any method known in the art including but not limited to, growth in culture tubes, shake flasks or bacterial fermentors. One preferred embodiment of the invention is propagation of host cells containing a recombinant expression vector in a fermentor as described in co-owned U.S. Pat. No. 5,851,802 and U.S. patent application Ser. No. 09/271,970, or by other means known in the art.

Other aspects and advantages of the present invention will be understood upon consideration of the following illustrative examples wherein Example 1 addresses the construction of novel isogenic arabinose transport-deficient strains that are transformed in Example 2 with a vector encoding a recombinant protein product. Example 2 addresses analysis of expression of an exemplary recombinant protein product, gelonin, in W3110, E220, E224 and E226 after arabinose induction by SDS-PAGE and ELISA. Example 3 addresses analysis of cell growth and gelonin protein product expression in E104, E221, E225 and E227 after arabinose induction.

EXAMPLE 1

Construction of Arabinose Transport-deficient Strains

Isogenic ΔaraFGH::kan and araE201 strains were constructed from E. coli W3110 (ATCC 27325) and E. coli E104 (deposited as ATCC 69009; ATCC 69008; ATCC 69101; ATCC 69102; ATCC 69103; ATCC 69104; ATCC 69331; ATCC 69332; ATCC 69333, each of which contains a gelonin-encoding plasmid). The resultant strains along with intermediate strains are shown in Table 1.

TABLE 1

Arabinose Proficient and Deficient Strains

| Strain | Parent or Reference | Relevant Genotype |
| --- | --- | --- |
| CW2553 | Horazdovsky and Hogg, 1989, Jour. of Bacter. 171: 3053–3059 | ΔaraFGH::kan araE201 |
| E104 | W3110/See, Example 1 | Δ(araBC)768 |
| W3110 | ATCC 27325 | |
| E220 | W3110/PTA-1524[A] | ΔaraFGH::kan |
| E221 | E104/PTA-1525[A] | ΔaraFGH::kan |
| E222 | W3310 | thyA |
| E223 | E104 | thyA |
| E224 | E222/PTA-1526[A] | araE201 |
| E225 | E223/PTA-1527[A] | araE201 |
| E226 | E224/E228/PTA-1528[A] | ΔaraFGH::kan araE201 |
| E227 | E229/PTA-1529[A] | ΔaraFGH::kan araE201 |
| E228 | E220 | ΔaraFGH::kan thyA |
| E229 | E221 | ΔaraFGH::kan thyA |

[A]Deposited with the American Type Culture Collection (ATCC) on Mar. 21, 2000.

Construction of E220 and E221

E220 and E221 were constructed by P1 transduction of W3110 and E104, respectively, with bacteriophage P1vir grown on E. coli CW2553 (Horazdovsky and Hogg, supra). For preparation of the P1 phage stock on E. coli CW2553, bacterial cells were inoculated into TYE (tryptone 15 g/L, yeast extract 10 g/L and NaCl 5 g/L) medium and grown for 6 hours. Cells were diluted 1:50 into TYE supplemented with 5 mM $CaCl_2$ and grown for an additional 90 minutes. A P1vir phage stock was diluted 1:1000 into a minimal salts solution (per liter: 21.4 g $K_2HPO_4$, 10.4 g $KH_2PO_4$, 13.6 g $(NH_4)_2SO_4$ and 0.3 g $MgSO_4$.7 $H_2O$), and 0.1 mL of phage was mixed with 0.2 mL of cells. The phage and cells were incubated at 37° C. for 20 minutes without shaking, then 3 mL of R soft agar (Miller, A Short Course in Bacterial Genetics, CSHL Press, 1992) was added and the mixture was plated onto R agar and grown overnight. Three mL of TYE was added to the top of the plate, and the TYE and soft agar mixture was scraped from the plate surface. Three drops of chloroform was added, the mixture were vortexed and the phage stock was separated from the agar by centrifugation. The titer of the resulting phage stock was approximately $4 \times 10^9$ phage/mL.

For transduction of W3110 and E104, each strain was grown overnight in TYE+5 mM $CaCl_2$. The cells in two mL of each culture were collected by centrifugation, suspended in 2 mL of 0.1 M $MgSO_4$, 0.005 mM $CaCl_2$, and incubated at 37° C. for 15 minutes. Cells (0.3 mL) and 0.2 mL of TYE+5 mM $CaCl_2$ were mixed with 0.1 mL of undiluted phage, phage that had been diluted 1:10 or 1:100, or dilution buffer only. Cells and phage were incubated for 20 minutes at 37° C., then 0.6 mL of 1 M sodium citrate was added followed by 6 mL of TYE. Transductants were grown for 4 hours at 37° C. prior to plating on TYE plates supplemented with kanomycin (50 mg/L). Colonies appeared on the plates with phage that had been diluted 1:10 and 1:100. No colonies appeared on the control plates. One kanomycin-resistant transductant of W3110 was selected as E220, and one kanomycin-resistant transductant of E104 was selected as E221.

Construction of E222, E223, E228 and E229

Because the araE201 allele can be co-transduced with the thyA gene, thyA derivatives of W3110, E104, E220 and E221 were identified by selection on trimethoprim plates (Miller, supra). Miminal glucose trimethoprim plates were prepared with 10 mg/L trimethoprim, and each strain was plated. Small colonies arising after approximately 4 days were restreaked onto trimethoprim plates and single colonies were selected. These single colonies were then restreaked on minimal plates, minimal plates supplemented with thymidine and trimethoprim plates. A thyA derivative of each strain was thereby identified as indicated in Table 1.

Construction of E224

E. coli E222 was transduced to ThyA+ with P1vir grown on CW2553. Cells were grown overnight in TYE+5 mM $CaCl_2$, suspended in 0.1 M $MgSO_4$, 0.005 M $CaCl_2$ and incubated with serial dilutions of phage in 0.6 mL. Cells and phage were incubated for 20 minutes at 37° C. followed by addition of 0.6 mL of 1 M sodium citrate and 6 mL of TYE. Transductants were grown for 1 hour at 37° C. then collected by centrifugation and suspended in 1 mL of a salt solution (per liter: 21.4 g $K_2HPO_4$, 10.4 g $KH_2PO_4$, 13.6 g $(NH_4)_2SO_4$ and 0.3 g $MgSO_4.7 H_2O$). Cells were plated onto glucose minimal plates and grown at 37° C. Ten candidate transductants were restreaked on minimal plates. Colonies arising from the restreak were tested for their phenotype of arabinose tetrazolium plates. E222 was white on arabinose tetrazolium plates (Ara$^+$) while seven of ten transductants were pink. Ara$^-$ strains are red on tetrazolium plates. One pink colony was selected as E224. These data demonstrate that the araE201 strains exhibit a partially Ara$^-$ phenotype. This phenotypic distinction could also be seen on MacConkey plates supplemented with 0.25% arabinose, on which E224 grew as pale pink colonies.

Construction of E226

A bacterial strain that is araE201 and ΔaraFGH was constructed from each of E224 and E228 yielding strains with identical genotypes. E224 was transduced to kanomycin resistance with a P1vir lysate from CW2553 and a single transductant was selected as E226. Similarly, E228 was transduced to ThyA$^+$ with a P1vir lysate from CW2553. From the two ThyA$^+$ transductants of E228, one candidate clone had the partial Ara$^-$ phenotype, i.e. pink colonies, on arabinose tetrazolium plates. This candidate was also selected as E226. Strain E226 prepared from either E224 or E228 had identical genotype and displayed the same phenotype on tetrazolium arabinose plates.

Construction of E227

While an araE201 derivative of E222 or E228 could be selected among ThyA$^+$ transductants by phenotypic selection on indicator plates, this approach could not be used for selection of an araE201 derivative of strains evolving from E104 since that strain is already Ara$^-$ owing to a deletion of the araBC region, Δ(araBC)768. Therefore, a different approach was necessary to select for this arabinose transport mutant in an arabinose minus background. Toward this end, E229 was transformed with plasmid pING3825, which encodes the gelonin protein under the inducible control of the araB promoter, and tetracycline resistant colonies were selected. E229 (pING3825) was then transduced to ThyA$^+$ with P1vir propagated on CW2553, and transductants were selected on minimal glucose plates supplemented with tetracycline. ThyA$^+$ transductants along with E220 (pING3825) and E226 (pING3825) were inoculated into TYE+tetracycline and grown overnight. Transductants and the controls were then diluted into 10 mL of medium and grown for approximately two hours to an $OD_{600}$ of about 0.4. Three mL of each culture was removed to a tube containing either 0.15 mL of 0.2% arabinose or 0.15 mL of 20% arabinose to a final arabinose concentration of 0.01 or 1%, respectively. Each culture was grown for 4.5 hours, and cells were removed by centrifugation. Fifteen microliters of the cell-free culture supernatant from five transductants and the E220 and E226 controls were evaluated by SDS-PAGE. The gel was stained with Coomassie colloidal blue, photographed and then stained with silver, FIG. 1. Two of the transductants produced very little recombinant gelonin after four hour induction with 0.01% arabinose as did the E226 control, while three others produced approximately as much gelonin as did the E220 control. In the cultures induced with 1.0% arabinose, no differences among the transductant expression levels were detected. The cells used to generate the sample in FIG. 1, lane 3, were chosen as E. coli E227 (pING3825). To select for a strain that had lost the plasmid, a culture of E227 (pING3825) was grown for 3 days in TYE at 37° C., then plated on TYE plates to isolate single colonies. Colonies were picked onto plates with and without tetracycline, and a colony was identified that had lost the plasmid. This strain was designated E227.

Construction of E225

E. coli E223 was transformed with plasmid pING3825, and colonies containing the plasmid were selected on plates containing tetracycline. E223 (pING3825) was transduced with P1vir grown on CW2553 and transductants capable of growth on minimal plates were selected. Individual colonies were screened for gelonin production after induction with 0.01% arabinose as outlined above for the selection of E227. A cell line that produced only a small quantity of gelonin compared to E220 (pING3825) and E104 (pING3825) and an amount similar to E227 (pING3825) was selected as E225 (pING3825). To identify a cell line that had lost the pING3825 plasmid, E227 (pING3825) was grown for 24 hours at 37° C., then set out at room temperature for three days. Viable cells in the culture were then plated on TYE medium and the resultant colonies were then picked onto plates with and without tetracycline, and a colony was identified that had lost the plasmid. This strain was designated E225.

EXAMPLE 2

Figure 2:
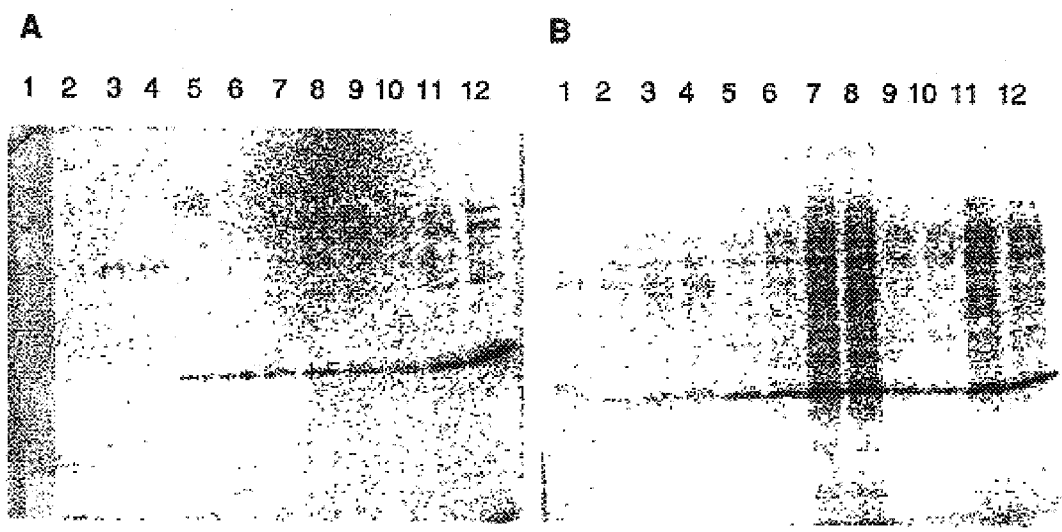
FIG. 2 shows Coomassie colloidal blue stained polyacrylamide gels that compare the cell-free culture supernatants from bacterial host cells induced with arabinose.
Figure 3:
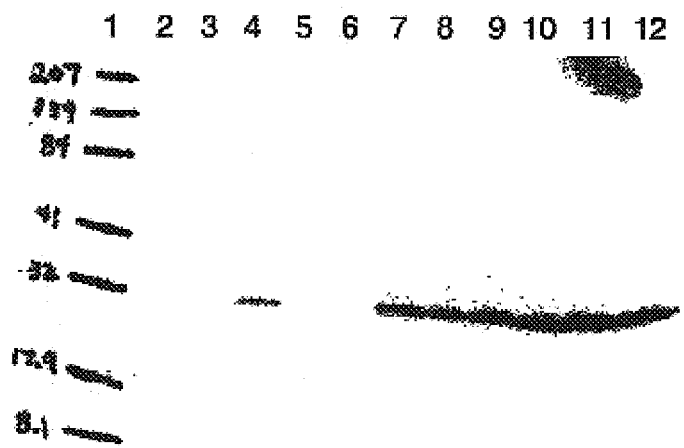
FIG. 3 shows a Western blot of induced and uninduced samples that compare the cell-free culture supernatants from bacterial host cells induced with arabinose.

SDS-PAGE and ELISA Analysis of Gelonin Expression in W3110, E220, E224 and E226 after Arabinose Induction Four isogenic strain (W3110, E220, E224 and E226) were transformed with pING3825. Each cell line was grown to an OD$_{600}$ of approximately 0.4, then aliquots of 2 mL of each culture were transferred to tubes supplemented with arabinose to 0, 0.01, 0.1 or 1%. Twenty eight tubes were set up, so that cells induced with 0, 0.01, 0.1 or 1% arabinose could be harvested at 4 hours post-induction and cells induced with 0.01, 0.1 and 1% arabinose could be harvested 18 hours post-induction. After the appropriate induction period of either 4 or 18 hours, cells were removed from the culture supernatant by centrifugation and each supernatant was filtered through a 0.2 μm filter before storage at 4° C. Ten microliters of each supernatant was evaluated by sodium dodecyl sulfate-polyacrylamide gel electrophoresis (SDS-PAGE). Samples from each supernatant were stained with Coomassie colloidal blue, FIG. 2. Some samples were also transferred to a PVDF membrane and detected with rabbit antibody to gelonin followed by a goat anti-rabbit peroxidase conjugate, FIG. 3. After induction with 0.01% arabinose for 4 hours, gelonin expression was detectable (faint band) in W3110 and E220 by Coomassie colloidal blue, FIG. 2A, lanes 1 and 2, and gelonin was easily detectable by Western blot analysis in E220, but none could be detected in the E224 or E226 samples at 4 hours by either technique. At 4 hours post-induction at 0.1% arabinose, no differences could be detected in the amount of gelonin expression in any of the samples, where a band of the size expected for gelonin was clearly present, FIG. 2A, lanes 5–8 and FIG. 3, lanes 7–9. At 4 hours post-induction with 1% arabinose, however, there was more expression evident in strains E224 and E226 than in either strain W3110 or E220 samples, FIG. 2A, lanes 9–12, and FIG. 3, lanes 10–12.

In the 18 hour induction samples, there was no apparent difference in the amount of gelonin present in any of the four samples induced with 0.01% arabinose, FIG. 2B, lanes 1–4. In direct contrast, there was much more gelonin in samples of E224 and E226 induced with either 0.1 or 1.0% arabinose than in samples of W3110 or E220. Enhanced expression of gelonin in the 1.0% arabinose at 4 hours and 0.1, FIG. 2B, lanes 5–8 (cp. lanes 7, 8 with lanes 5, 6), or 1.0%, FIG. 2B, lines 9–12 (cp. lanes 11, 12, with lane 9, 10), arabinose at 18 hours in E224 and E226 demonstrating the advantage of recombinant gene expression in transport-deficient bacterial host cells. Less bacterial growth inhibition after arabinose induction was evident in E224 and E226 cultures, and likely resulted in greater cell accumulation of recombinant proteins. More cells in the resulting samples thereby resulted in more gelonin expression in the culture. These data demonstrate that an intact AraE transport system is required for low level induction of a recombinant protein from a moderate copy plasmid by 0.01% arabinose within 4 hours, while expression at 18 hours is identical in both araE$^-$ and araE$^+$ strains. These data also show that cells deficient in AraF induce the recombinant product similarly to the wild type strain under all experimental conditions tested.

The same samples that were evaluated by SDS-PAGE were also evaluated by ELISA. Wells were coated with rabbit antibody to gelonin before addition of induced samples. Gelonin bound in each well was detected with biotinylated rabbit antibody to gelonin, and the biotin in each well was detected with a streptavidin horseradish peroxidase conjugate. Table 2 shows the results of this first ELISA assay.

TABLE 2

Gelonin detected by ELISA after 4 hours of induction (ng/ml)

| Strain | Arabinose Concentration | | |
|---|---|---|---|
| | 0.01% | 0.1% | 1.0% |
| W3110 | 44.7 | 101 | 165 |
| E220 | 42 | 81 | 124 |
| E224 | 3.6 | 254 | 121 |
| E226 | 2.6 | 141 | 219 |

E220 and W3310 respond similarly to arabinose induction, while the araE201 and araE201 ΔaraFGH strains E224 and E226, respectively, produce much less gelonin at 0.01% arabinose but approximately as much or more gelonin at 0.1% and 1.0% arabinose. The ELISA data also demonstrate that the araF$^-$ strain E220 produces slightly less recombinant protein than does W2110.

In a separate experiment, E. coli E220 and E226 were evaluated temporally for the expression of gelonin after induction with 0.01% and 1.0% arabinose. After induction at either 0.1% or 1.0% arabinose concentration, samples were removed at 1.25, 3 and 4.5 hours after induction, and the amount of gelonin appearing in the cell-free culture supernatant was evaluated by ELISA. The data from this experiment are shown in Table 3.

TABLE 3

Gelonin detected by ELISA after induction with arabinose (ng/mL)

| Time after Induction | 0.01% arabinose | | 1.0% arabinose | |
|---|---|---|---|---|
| | E220 | E226 | E220 | E226 |
| 1.25 Hours | <1.05† | <1.05 | 2.6 | 4.8 |
| 3.0 Hours | 8.6 | 1.4 | 35.6 | 131 |
| 4.5 Hours | 9.5 | 2.1 | 126 | 156 |

†limit of detection in this assay was 1.05 ng/mL

These data further demonstrate that, at the low arabinose concentration (0.01%), E226 is less inducible than is E220. However, after induction at the higher arabinose concentration, E226 accumulates more product than E220. These data also demonstrate that E226 more rapidly accumulates gelonin than does E220. The samples described in Table 3 were also evaluated by Western blotting. Samples were separated by SDS-PAGE and transferred to a PVDF membrane. The amount of gelonin in each lane was detected with rabbit antibody to gelonin followed with a goat anti-rabbit peroxidase conjugate. The Western data confirmed the ELISA data at 0.01% arabinose showing that arabinose, no or very little induction of gelonin occurred in E226. At 1.0% arabinose induction, more product appeared in the E226 strain than in E220 at the 3 and 4.5 hour time points, and even a small amount of gelonin appeared in the 1.0% arabinose sample after 1.25 hours.

EXAMPLE 3

Analysis of Cell Growth and Gelonin Expression in E104, E221, E225 and E227 after Arabinose Induction Four Δ(araBD)768 bacterial cell lines (E104, E221, E225 and E227) each containing pING3825 were grown in TYE medium to an OD of approximately 0.4 and induced in 2.15 mL aliquots with arabinose to 0, 0.1, 1 and 10 mM (10 mM 0.15%; 1 mM 0.015%; 0.1 mM 0.0015%). At 4 hours post-induction, the $OD_{600}$ of a 1:5 dilution of each culture was determined, then the culture was centrifuged to remove cells and the filtered supernatant was placed at −20° C. for subsequent evaluation by ELISA. Likewise, at 17 hours post-induction, the $OD_{600}$ of a 1:10 dilution of each culture was determined, then the culture was centrifuged to remove cells and the filtered supernatant was placed at −20 C for subsequent evaluation by ELISA. Table 4 illustrates the culture $OD_{600}$ for each sample.

TABLE 4

Optical Density of E104, E221, E225 and E227 cultures induced with arabinose

| Strain | mM arabinose | OD (4 hours) | OD (17 hours) |
| --- | --- | --- | --- |
| E104 | 0 | 1.795 | ND |
|  | 0.1 | 1.565 | 3.27 |
|  | 1.0 | 0.745 | 0.91 |
|  | 10 | 0.825 | 0.74 |
| E221 | 0 | 1.815 | ND |
|  | 0.1 | 1.975 | 3.32 |
|  | 1.0 | 0.815 | 1.23 |
|  | 10 | 0.665 | 0.93 |
| E225 | 0 | 2.19 | ND |
|  | 0.1 | 1.78 | 4.34 |
|  | 1.0 | 1.55 | 2.3 |
|  | 10 | 0.905 | 1.04 |
| E227 | 0 | 2.12 | ND |
|  | 0.1 | 1.89 | 3.56 |
|  | 1.0 | 1.615 | 3.26 |
|  | 10 | 1.025 | 1.25 |

ND = not determined

Each sample was evaluated by ELISA to determine the amount of gelonin that had accumulated in the culture supernatant after induction with arabinose. The results from this ELISA are shown in Table 5.

TABLE 5

Gelonin detected by ELISA after induction with arabinose (ng/mL)

| | | Gelonin ng/ml | |
| --- | --- | --- | --- |
| Strain | mM arabinose | 4 hours | 17 hours |
| E104 | 0 | 0.019 | ND |
|  | 0.1 | 0.67 | 1.1 |
|  | 1.0 | 44.5 | 115.8 |
|  | 10 | 30.2 | 111.6 |
| E221 | 0 | 0.014 | ND |
|  | 0.1 | 0.022 | .266 |
|  | 1.0 | 26.2 | 103.6 |
|  | 10 | 20.6 | 77 |
| E225 | 0 | 0.016 | ND |
|  | 0.1 | 0.067 | 2.45 |
|  | 1.0 | 8.2 | 122 |
|  | 10 | 29.4 | 101.6 |
| E227 | 0 | 0.011 | ND |
|  | 0.1 | 0.015 | 0.131 |
|  | 1.0 | 7.0 | 85 |
|  | 10 | 34 | 103.8 |

ND - Not determined the data in Tables 4 and 5 demonstrate that the arabinose transport-deficient strains are less growth-inhibited by arabinose after induction than E104, yet are capable of gelonin expression to approximately the same or greater level than E104 with 10 mM arabinose after both 4 and 17 hours. Because passive diffusion of arabinose into host cells is the only remaining mechanism for the intracellular accumulation of arabinose in E227, this strain apparently is less growth-inhibited at low arabinose concentrations than E104, and also produces less gelonin at low arabinose concentrations. The phenotypic effects of the AraFGH deletion and AraE mutation can be seen independently in this set of induced bacterial host strains. E225 (araE201) produces more gelonin at either 4 or 18 hours at 0.1 mM arabinose than does E221 or E227 (both are ΔaraFGH), thereby demonstrating that the AraFGH transport system is most responsive at very low arabinose concentrations. Similarly, E225 and E227 produce less gelonin at 1.0 mM arabinose at 4 hours, demonstrating the importance of the AraE transport system at this higher arabinose concentration. In addition, it appears that the effects of the arabinose transport deficiency in AraFGH and AraE transporters are additive. The double mutant is less inhibited in cell growth at high arabinose concentration than either of the single mutants, though the AraE⁻ and AraEFGH⁻ strains produce about equal amounts of gelonin at 1–10 mM arabinose. At low arabinose concentration (0.1 mM), however, the double mutant produces only slightly less gelonin than does the araF single mutant. All strains show similar, full and quick induction at 10 mM arabinose where presumably the transport systems are not essential for accumulation of intracellular arabinose. At the lower concentrations of arabinose in the medium, however, differences appear between wild type and mutant strains. AraE strains are not as completely induced by 4 hours as are wild type or AraFGH strains.

The data in the examples demonstrate that arabinose transport-deficient strains containing vectors encoding recombinant protein products are particularly useful as hosts for the expression of recombinant protein products under the inducible control of the araB promoter. Less bacterial cell growth inhibition (e.g., higher cell numbers), higher recombinant protein product expression, and directly regulatable expression, including synchronous induction of expression by arabinose, of recombinant protein product are different aspects and surprising advantages of the present invention. During growth in a fermentor of transport-deficient host cells that contain a recombinant expression vector, bolus addition of an inducer, such as arabinose, to induce the culture is expected to inhibit cell growth less than in an otherwise equivalent or comparable culture of transport-proficient host cells. Thus, improved recombinant protein product production, including higher yield of cells and/or product, is expected using the methods and bacterial host cells of the present invention.

The foregoing examples are presented by way of example and are not intended to limit the scope of the invention as set forth in the appended claims.

What is claimed is:

1. A method for producing a recombinant protein product under the control of an inducible promoter, wherein the inducible promoter is an araB promoter, comprising: (a) introducing an expression vector encoding a recombinant protein product under the control of the inducible promoter into an *E. coli* bacterial host cell that is genetically deficient in at least one system for active transport of an arabinose inducer of the inducible promoter, wherein the system is encoded by an araE gene or araFGH genes; and (b) inducing expression of the product with the inducer.

2. The method of claim 1, wherein the host cell cannot grow on arabinose.

3. The method of claim 1, wherein the host cell is deficient in the low affinity arabinose transport system encoded by the araE gene.

4. The method of claim 1, wherein the host cell is deficient in the high affinity arabinose transport system encoded by the araFGH genes.

5. The method of claim 1, wherein the host cell is deficient in both the high affinity arabinose transport system encoded by the araFGH genes and the low affinity arabinose transport system encoded by the araE gene.

6. The method of claim 1 further comprising a step of recovering the product from the induced host cells.

7. A method of producing a recombinant protein product under the control of an inducible promoter, wherein the inducible promoter is an araB promoter, and synchronously inducing expression of the product comprising: (a) culturing *E. coli* bacterial host cells that are genetically deficient in at least one system for active transport of an arabinose, inducer of the inducible promoter into the host cells, wherein the system is encoded by an araE gene or araFGH genes, wherein the host cells contain an expression vector encoding a recombinant protein product under the control of the inducible promoter; and (b) inducing expression of the product with a concentration of inducer effective to synchronously induce the expression of the product by the host cells.

8. The method of claim 7, wherein the host cells cannot grow on arabinose.

9. The method of claim 7, wherein the host cells are deficient in the low affinity arabinose transport system encoded by the araE gene.

10. The method of claim 7, wherein the host cells are deficient in the high affinity arabinose transport system encoded by the araFGH genes.

11. The method of claim 7, wherein the host cells are deficient in both the high affinity arabinose transport system encoded by the araFGH genes and the low affinity arabinose transport system encoded by the araE gene.

12. A method of reducing bacterial cell growth inhibition induced by an arabinose inducer of an inducible promoter, wherein the inducible promoter is an araB promoter, comprising: (a) culturing *E. coli* bacterial host cells that are genetically deficient in at least one system for active transport of the inducer into the host cells, wherein the system is encoded by an araE gene or araFGH genes, wherein the host cells contain an expression vector encoding a recombinant protein product under the control of the inducible promoter; and (b) inducing expression of the product with a concentration of inducer effective to induce the expression of the product in the host cells, but not effective to inhibit growth of the cells as compared with that in transport-proficient cells.

13. The method of claim 12, wherein the host cells cannot grow on arabinose.

14. The method of claim 12, wherein the host cells are deficient in the low affinity arabinose transport system encoded by the araE gene.

15. The method of claim 12, wherein the host cells are deficient in the high affinity arabinose transport system encoded by the araFGH genes.

16. The method of claim 12, wherein the host cells are deficient in both the high affinity arabinose transport system encoded by the araFGH genes and the low affinity arabinose transport system encoded by the araE gene.

17. A method of increasing yield of a recombinant protein product comprising: (a) culturing *E. coli* bacterial host cells that are genetically deficient in at least one system for active transport of an arabinose inducer of an inducible promoter, wherein the inducible promoter is an araB promoter, wherein the system is encoded by an araE gene or araFGH genes, and wherein the host cells contain an expression vector encoding the recombinant protein product under the control of the inducible promoter; and (b) inducing expression of the product with a concentration of inducer effective to increase the yield of the host cells or the product.

18. The method of claim 17, wherein the yield of the host cells and the product is increased.

19. The method of claim 17, wherein the host cells cannot grow on arabinose.

20. The method of claim 17, wherein the host cells are deficient in the low affinity arabinose transport system encoded by the araE gene.

21. The method of claim 17, wherein the host cells are deficient in the high affinity arabinose transport system encoded by the araFGH genes.

22. The method of claim 17, wherein the host cells are deficient in both the high affinity arabinose transport system encoded by the araFGH genes and the low affinity arabinose transport system encoded by the araE gene.

23. A method for producing a recombinant protein product under the control of an inducible promoter, wherein the inducible promoter is an araB promoter, comprising: (a) culturing an *E. coli* bacterial host cell that is genetically deficient in at least one system for active transport of an arabinose inducer of the inducible promoter into the host cell, wherein the system is encoded by an araE gene or araFGH genes, wherein the host cell contains an expression vector encoding a recombinant protein product under the control of the inducible promoter; and (b) inducing expression of the product with the inducer.

24. The method of claim 23, wherein the host cell cannot grow on arabinose.

25. The method of claim 23, wherein the host cell is deficient in the low affinity arabinose transport system encoded by the araE gene.

26. The method of claim 23, wherein the host cell is deficient in the high affinity arabinose transport system encoded by the araFGH genes.

27. The method of claim 23, wherein the host cell is deficient in both the high affinity arabinose transport system encoded by the araFGH genes and the low affinity arabinose transport system encoded by the araE gene.

28. The method of claim 7, 12, 17, or 23 further comprising a step of recovering the product from the induced host cells.

* * * * *